United States Patent [19]

Calvin et al.

[11] 4,162,308

[45] Jul. 24, 1979

[54] WATER SOLUBLE EXTRACTS OF CERTAIN MARINE RED ALGAE AND PROCESSES FOR USE THEREOF

[76] Inventors: Natasha I. Calvin; Robert J. Ellis, both of Box 112, Auke Bay, Ak. 99821

[21] Appl. No.: 894,831

[22] Filed: Apr. 10, 1978

[51] Int. Cl.$^2$ ...................... A61K 35/78; A61K 31/70
[52] U.S. Cl. ..................................... 424/195; 424/180
[58] Field of Search .......................................... 424/195

[56] References Cited

FOREIGN PATENT DOCUMENTS

| 7020953 | 7/1970 | Japan | 424/195 |
| 7318446 | 6/1973 | Japan | 424/195 |
| 331833 | 9/1958 | Switzerland | 424/195 |

OTHER PUBLICATIONS

Frank et al., Antimicrobial Agents & Chemotherapy, Oct. 1974, pp. 524–525, vol. 6, No. 1 pub. by Amer. Soc. for Microbiology.
Ehresmann et al., J. Phycol. 13, pp. 37–40 (1977) accepted Aug. 30, 1976.
Takemoto et al., Proc. Soc. Exp. Biol. and Med., vol. 116 (1964) pp. 140–144, "Herpes Virus and Acid Polysaccharides".
The Dispensatory of the U.S.A., 24th ed. (1947) pp. 28–30, published by J. B. Lippincott Co., Phila. Pa.

Primary Examiner—Donald B. Moyer
Attorney, Agent, or Firm—Christensen, O'Connor, Johnson & Kindness

[57] ABSTRACT

A water soluble extract from marine red alga selected from the group consisting of *Turnerella mertensiana, Schizymenia epiphytica, Turnerella pennyi* and mixtures thereof has been found effective to inhibit the growth of herpes simplex virus, type 1 and type 2, and herpes zoster, and to relieve the pain caused by infection attributable to such virus.

4 Claims, No Drawings

WATER SOLUBLE EXTRACTS OF CERTAIN MARINE RED ALGAE AND PROCESSES FOR USE THEREOF

BACKGROUND OF THE INVENTION

The present invention relates to water soluble extracts of certain red algae, and more particularly to the water soluble extract of the alga *Turnerella mertensiana* and related species of algae, and to the processes for producing an aqueous extract from the algae, as well as processes for administering the water soluble extract for the treatment of certain viral infections attributable to herpes simplex virus, type 1 and type 2 and herpes zoster.

It has been suggested that certain marine red algae found off the California coast have some inhibiting activity on the replication of types 1 and 2 herpes simplex virus (hereinafter referred to as the herpes virus). See, for example, the articles by Ehresmann, D. W., et al., "Inhibition of Herpesvirus Replication by Marine Algae Extracts," *Anti-microbial Agents and Chemotherapy*, Vol. 6, No. 1, October, 1974, pp. 524 and 525, and "Antiviral Substances from California Marine Algae," *J. Phycol.*, Vol. 13, pp. 37-40, 1977.

Although the antiviral activity of such marine red algae has been noted in literature, the antiviral activity of such algae has proven to be of limited efficacy for the inhibition of replication of the herpes virus. For instance, there has been no demonstrated effectiveness of such algae against vesicular stomatitis or for relief of pain. Studies have indicated that other marine flora and fauna may also have antiviral activity. Prior to the present discovery, however, no readily available, simply processible and usable antiviral agent has been discovered that yields a very high degree of antiviral activity with respect to the herpes virus or that relieves pain.

SUMMARY OF THE INVENTION

In accordance with the discoveries disclosed herein, it has been found that the water soluble extract of *Turnerella mertensiana*, *Schizymenia epiphytica*, *Turnerella pennyi* or mixtures thereof are extremely effective for the treatment of herpes type viruses, that is, to inhibit replication of the virus. Moreover, it has surprisingly been found that such water soluble extracts are extremely effective in relieving pain caused by herpetic infections upon topical application. The water soluble extract of the aforementioned algae is also effective in treating and relieving the pain of herpetic lesions of the skin, genital herpes infections and of herpes zoster. It is also believed that the water soluble extract of the above-identified algae is effective in the prevention or treatment of varicella (chicken pox) lesions, closely related to herpes zoster, prevention or treatment of herpetic infection in the fetus or newly born child, treatment of herpetic encephalitis, and of other herpetic diseases.

DETAILED DESCRIPTION OF THE INVENTION

It has been found that a water soluble extract from the marine red alga *Turnerella mertensiana* (Postels and Ruprecht) Schmitz, 1889, is extremely effective to inhibit the replication of the herpes virus, as well as for almost immediately relieving pain caused by herpetic infections. *T. mertensiana* has been identified in the reproductive stage in accordance with the description of Schmitz, 1889. *T. mertensiana* is indigenous to the Washington, British Columbia, Canada and Alaska Pacific coastal waters. The alga identified as *Schizymenia epiphytica* is believed to be the same alga as the *T. mertensiana* when both are in a nonreproductive stage, as what has been often identified as *Schizymenia epiphytica* in Alaska is virtually identical to and indistinguishable from *T. mertensiana* when both are in the nonreproductive stage. It is therefore believed that a water soluble extract from the *Schizymenia epiphytica* has an efficacy for the treatment of herpes virus identical to that of the *T. mertensiana*. It is also believed that the circumboreal species identified as *Turnerella pennyi* is identical to the *T. mertensiana* species. Thus the water soluble extract from the *T. pennyi* species of red alga is believed to have the same efficacy as the *T. mertensiana* also. Therefore, a water soluble extract from any one of the aforementioned three red marine algae or mixtures thereof is effective to inhibit replication of the herpes virus and relieve the pain caused by herpetic infection.

There are believed to be at least two active components in the water soluble extract of the algae. One of the components is active to almost completely inhibit replication of the herpes virus. The other active component relieves the pain associated with herpetic infections. The active components, which have not been identified, are derived by aqueous extraction from the algae.

The active components can be extracted from the algae by first gathering the fresh algae from its salt water environment and washing it in clean tap or distilled water. The algae is then preferably dried at room temperature to a water content on the order of 10% by weight. The algae can be stored in air dried form or can be further dried in an oven at a relatively low, nondestructive temperature in the range of from 100° F. to 120° F., and preferably on the order of 120° F. The algae can then be comminuted by any suitable device (such as a blender, mortar and pestle, or commercially available grinders,) to a fine powder and stored for an indefinite time in dry form. The water soluble active components are extracted by mixing the algal powder with water, and maintaining contact between the powder and water with frequent stirring or shaking for on the order of 30 minutes or more. Preferably the supernatant fluid is then separated from the algal residue. The active ingredients are contained in the supernatant fluid in concentrated form. Alternatively, the algae need not be dried prior to the water extraction step, but is preferably washed free of salt water. After washing, the algae can be comminuted in its freshly washed form or can be frozen and thereafter comminuted by any suitable device, such as by subjecting the algae to sonic vibrations in water.

It is preferred that the dried algal powder be extracted to provide an effective concentration of the active components for topical application by combining the powder with water in proportions on the order of from 100 parts by weight water to 1 part by weight of powder (50 mg of powder to 5 ml of water). If the algae were not first dried, the amount of water employed for extraction can be adjusted to compensate for the natural water content of the plant, which is on the order of 90% by weight.

The aqueous extract is preferably sterilized by passing it through a conventional millipore filter or other suitable system for separating bacterial contaminants. In addition, or alternatively, the water soluble extract can be mixed with suitable preservatives such as glycerine or ethanol in weight proportions on the order of one part by weight of extract to one part by weight of preservative. In the sterilized and preserved form, the extract is maintained in its active state for an indefinite period when kept in a stoppered or closed container.

It has been found that the water soluble extract from the aforementioned marine red algae is effective to inhibit replication of the herpes virus in humans affected with the same, especially when the virus manifests itself in the form of herpetic gingiva stomatitis, herpes zoster, herpetic lesions, such as cold sores, and genital herpetic infections. It is also believed that the active compositions of matter in the water soluble extract are efficacious to inhibit replication of the herpes virus manifesting itself in herpetic infections of the eye (herpes keratitis), varicella lesions, and herpetic infections in the fetus and newly born children. The water soluble extract from the aforementioned marine red algae has been found to be more effective when the extract is applied soon after the viral infection manifests itself in the form of tenderness, subcutaneous inflammation, or a surface lesion on the skin or other tissue, but most preferably before the lesion develops.

The method of treatment utilizing the water soluble extract of the present invention can generally be by topical application of the water soluble algal extract. For the treatment of cold sores or fever blisters attributable to the herpes virus, the water soluble extract is directly contacted with the infected area. Normally the frequency of application is at 20 minute to 30 minute intervals during the first few hours of treatment. Thereafter, the affected areas can be treated topically at one hour intervals or as often as necessary to maintain continuity of pain relief. When the water soluble algal extract of the present invention is mixed in weight proportions on the order of 1:1 with glycerine or with ethanol, the efficacy of the algal extract remains substantially the same.

For herpetic infections of the mouth and throat (for example, canker cores and herpetic vesicular stomatitis), the same topical application as for cold sores is preferred. It is further preferred that the water soluble algal extract prepared as set forth above be used without dilution with glycerine or ethanol. For limited outbreaks (when only a few lesions appear on the skin), the extract is applied topically with a swab or other suitable applicator. The same intervals for application are used as were used for cold sores. For extensive outbreaks of herpetic infection, it is preferred that the solution is used as a mouthwash. Again, the same application intervals are preferred as for cold sores.

When the water soluble algal extract is used to treat external genital herpes, the extract is applied to the affected area with a swab or other suitable applicator. Again, the same intervals for application are used as for cold sores. For the treatment of herpes zoster, the undiluted extract is again preferred for application at the same intervals.

It is also believed that the active components of the water soluble extract can be used for systemic treatment of nonsurface manifestations of herpes viruses, such as herpetic encephalitis. Such treatment can be effected by using purified extracts of the active components in a suitable carrier administered intravenously, by inhalation or by oral ingestion to a person infected with the herpes virus.

EXAMPLES

The following Examples are intended to illustrate the efficacy of the water soluble algal extract, as well as to instruct one of ordinary skill in the art how to extract and use the active components from the marine red algae identified above. The Examples are not intended to in any way limit the scope of the disclosed invention.

EXAMPLE I

Red marine algae identified as *Turnerella mertensiana* is dried for 8 to 12 hours at room temperature. Thereafter, the partially dried algae is further dried for about 10 minutes at 120° F. in an oven. The dried algae is then ground to a powder with a mortar and pestle. 50 mg portions of the algal powder are placed in each of 15 5 ml vials. To prepare the powder for application, the contents of a vial are mixed with about 1 oz of distilled water, stirred and allowed to set for about 30 minutes to yield an aqueous solution of the water soluble algal extract.

A human having a sore mouth, sore throat, numerous white lesions, many of which were vesicular, throughout the oral soft tissue (tongue, gingivae, floor of the mouth, hard and soft palate, mucosa, pharynx and lips) was treated three days after the onset of the first symptoms. The patient had no prior history of lesions of this nature. The lesions were diagnosed as primary herpetic gingiva stomatitis. The patient was treated with the aqueous solution of the water soluble extract from the algal powder prepared as described above with distilled water. The patient was treated orally by placing the 1 oz solution in the patient's mouth and having the patient thoroughly agitate the solution in her mouth and throat. About one ounce of the solution of the algal extract prepared from one vial of the powder was agitated in the mouth area per hour for the first day of treatment. Nine ounces of the solution of the algal extract prepared from nine vials of the algal powder were used during the first day of treatment.

During the first day of treatment, the following observations were made: pain from the lesions subsided significantly during the first hour after treatment; swelling in the throat was reduced and soreness was almost completely gone after the first day of treatment; gingiva on palate area was still sore to touch; one-third of the lesions on lip were dried up and appeared to be healing. During the second day one ounce of the solution of the water soluble extract prepared from one vial of the algal powder was orally administered to the patient three times at about 2 hour intervals. The following observations were made during the second day of treament: the pain of the lesions was almost completely gone; many lesions appeared to be healing; the throat was no longer sore or swollen. During the third day three vials of the algal powder were extracted as above and were again used for treatment in the same manner as on the second day. The following observations were made on the third day: the pain of the lesions was gone; all lesions appeared to be healed or were healing; and the throat region was normal, with no swelling. The normal course of this disease when untreated or treated by another method is about 14 days.

EXAMPLE II

The procedure of Example I was repeated on a second patient with the exception that one vial containing 500 mg of the algal powder was employed each day.

The patient mixed the powder with about 60 ml of water, allowed it to set for about 30 minutes, then swished about 5 to 10 ml of aqueous solution of the algal extract throughout the mouth. The procedure was repeated four times at one hour intervals for the first day. After the first day's treatment, the pain of the lesions had significantly subsided. During the second day, the treatment was continued as during the first day. During the second day, there was little discomfort from the lesions and only a few active lesions remained. During the third day of treatment, all lesions appeared to be healing and there was no patient discomfort. The treatment with the algal extract was therefore discontinued on the third day.

Although the present invention has been described in relation to a preferred embodiment, it is to be understood that one of ordinary skill may make various changes, substitutions of equivalents and other alterations without departing from the scope of the invention as disclosed. It is therefore intended that the grant of Letters Patent hereon be limited only by the definition contained in the appended claims and equivalents thereof.

The embodiments of the invention in which an exclusive property or privilege is claimed are defined as follows:

1. A method of treating and relieving pain of herpetic virus infections in humans comprising the steps of:
   intimately contacting the surface region directly infected with said virus with a water soluble extract of a marine red algae selected from the group consisting of *Turnerella mertensiana, Schizymenia epiphytica* and *Turnerella pennyi*, and mixtures thereof.

2. The method of claim 1 wherein said alga consists essentially of *Turnerella mertensiana*.

3. The method of claim 1 wherein said alga consists essentially of *Schizymenia epiphytica*.

4. The method of claim 1 wherein said alga consists essentially of *Turnerella pennyi*.

* * * * *